US011137395B1

United States Patent
Huang et al.

(10) Patent No.: US 11,137,395 B1
(45) Date of Patent: Oct. 5, 2021

(54) SARS-COV-2 (COVID-19) SPIKE-AXL BINDING ASSAY

(71) Applicant: RayBiotech Life, Inc., Peachtree Corners, GA (US)

(72) Inventors: Ruo-Pan Huang, Alpharetta, GA (US); Tuhin Das, Peachtree Corners, GA (US); Hao Tang, Duluth, GA (US); Shuhong Luo, Duluth, GA (US); Jianmin Fang, Athens, GA (US)

(73) Assignee: RayBiotech Life, Inc., Peachtree Corners, GA (US)

( * ) Notice: Subject to any disclaimer, the term of this patent is extended or adjusted under 35 U.S.C. 154(b) by 0 days.

(21) Appl. No.: 17/348,153

(22) Filed: Jun. 15, 2021

Related U.S. Application Data

(60) Provisional application No. 63/142,266, filed on Jan. 27, 2021.

(51) Int. Cl.
*G01N 33/543* (2006.01)

(52) U.S. Cl.
CPC . *G01N 33/54393* (2013.01); *G01N 2333/165* (2013.01); *G01N 2333/908* (2013.01); *G01N 2333/91205* (2013.01)

(58) Field of Classification Search
CPC ... G01N 33/54393; G01N 2333/91205; G01N 2333/908; G01N 2333/165
See application file for complete search history.

(56) References Cited

PUBLICATIONS

Esparza et al. "High affinity nanobodies block SARS-CoV-2 spike receptor binding domain interaction with human angiotensin converting enzyme." Scientific Reports. Publ. Nature Research. Iss. 10, Article No. 22370 (Dec. 22, 2020). https://doi.org/10.1038/s41598-020-79036-0 (Year: 2020).*
Aubin Moutal et al., "SARS-CoV-2 spike protein co-opts VEGF-A/ neuropilin-1 receptor signaling to induce analgesia", Pain. Jan. 2021;162(1):243-252. doi: 10.1097/j.pain.0000000000002097. PMID: 33009246; PMCID: PMC7737878.
U.S. Appl. No. 17/141,837, filed Jan. 5, 2021.
U.S. Appl. No. 17/197,216, filed Mar. 10, 2021.
U.S. Appl. No. 17/350,718, filed Jun. 17, 2021.
RayBio® COVID-19 S-Protein (S1RBD) ELISA Kit Protocol, www.RayBiotech.com/ELISA-Kits, Catalog #: ELV-COVID19S1, User Manual Last revised Jun. 14, 2021.
RayBio® COVID-19 Spike-AXL Binding Assay Kit I, For screening COVID-19 drugs and antibodies targeting the Spike-AXL protein interaction, catalog Nos. CoV-AXLS1-1 (1 plate kit) CoV-AXLS1-2 (2 plate kit) CoV-AXLS1-5 (5 plate kit), User Manual Last revised: Apr. 27, 2021, www.RayBiotech.com.

(Continued)

*Primary Examiner* — Jennifer Wecker
*Assistant Examiner* — Michael Paul Shimek
(74) *Attorney, Agent, or Firm* — Thomas | Horstemeyer, LLP

(57) ABSTRACT

The present disclosure an ELISA-based assay that uses a glycosylated s1F polypeptide fragment derived from the SARS-CoV-2 spike protein (Covid-19) spike protein, the N-terminal domain of which has affinity for the tyrosine-protein kinase receptor UFO (AXL). The S1F polypeptide can be generated by expression of an encoding nucleic acid by a human cell expression system resulting in glycosylation of the expressed S1F polypeptide at least at the N343 N-glycosylation site thereof, and which surprisingly and significantly increases the affinity of the S1F for AXL, provides a significant increase in the sensitivity of the assay compared to other known assays. Further the AXL polypeptide can be glycosylated, which further increases the affinity for S1F and AXL to each other.

9 Claims, 10 Drawing Sheets

Specification includes a Sequence Listing.

(56) References Cited

PUBLICATIONS

RayBio® Custom ELISA Kit, Catalog #: EL-PRELIM, User Manual Last revised Feb. 6, 2020, www.RayBiotech.com.
RayBio® Human ACE-2 ELISA Kit, Catalog #: ELH-ACE2, User Manual Last revised Jun. 14, 2021, www.RayBiotech.com.

* cited by examiner

S1F Pre-coated on plate ← S1F

← AXL
← Sample

Sample and Axl compete for binding to S1F

Unbound Axl washed off

Color substrate

*Fig. 4*

S1F (Enzyme-Treated) in AXL-coated S1F Binding assay

*Fig. 6A*

Effect of Deglycosylated S1F in AXL-S1F Binding Assay

Fig. 7

AXL-S1F Binding Assay

Effect of Deglycosylated AXL in S1F-AXL Binding

*Fig. 9*

SEQUENCE LISTING

```
<160> NUMBER OF SEQ ID NOS: 4

<210> SEQ ID NO 1
<211> LENGTH: 1273
<212> TYPE: PRT
<213> ORGANISM: Homo sapiens
<220> FEATURE:
<221> NAME/KEY: misc_feature
<223> OTHER INFORMATION: SARS-CoV-2 Covid S1F

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300
```

```
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720
```

-continued

```
Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
        1010                1015                1020

Leu Ala Ala Thr Lys Met Ser Glu Cys Val Leu Gly Gln Ser Lys
        1025                1030                1035

Arg Val Asp Phe Cys Gly Lys Gly Tyr His Leu Met Ser Phe Pro
        1040                1045                1050

Gln Ser Ala Pro His Gly Val Val Phe Leu His Val Thr Tyr Val
        1055                1060                1065

Pro Ala Gln Glu Lys Asn Phe Thr Thr Ala Pro Ala Ile Cys His
        1070                1075                1080

Asp Gly Lys Ala His Phe Pro Arg Glu Gly Val Phe Val Ser Asn
        1085                1090                1095

Gly Thr His Trp Phe Val Thr Gln Arg Asn Phe Tyr Glu Pro Gln
        1100                1105                1110

Ile Ile Thr Thr Asp Asn Thr Phe Val Ser Gly Asn Cys Asp Val
        1115                1120                1125
```

-continued

```
Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Ser Glu Pro
    1250                1255                1260

Val Leu Lys Gly Val Lys Leu His Tyr Thr
    1265                1270

<210> SEQ ID NO 2
<211> LENGTH: 894
<212> TYPE: PRT
<213> ORGANISM: Homo sapiens
<220> FEATURE:
<221> NAME/KEY: misc_feature
<223> OTHER INFORMATION: Human Axl isoform 1

<400> SEQUENCE: 2

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205
```

```
Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
                260                 265                 270

Ala Gly Glu Pro Asp Pro Pro Glu Pro Leu Thr Ser Gln Ala Ser
                275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
                340                 345                 350

Trp Gln Glu Pro Arg Ala Pro Leu Gln Gly Thr Leu Leu Gly Tyr Arg
                355                 360                 365

Leu Ala Tyr Gln Gly Gln Asp Thr Pro Glu Val Leu Met Asp Ile Gly
370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
                420                 425                 430

Pro Val His Gln Leu Val Lys Glu Pro Ser Thr Pro Ala Phe Ser Trp
                435                 440                 445

Pro Trp Trp Tyr Val Leu Leu Gly Ala Val Val Ala Ala Ala Cys Val
450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
                500                 505                 510

Leu Asn Ser Leu Gly Ile Ser Glu Glu Leu Lys Glu Lys Leu Arg Asp
                515                 520                 525

Val Met Val Asp Arg His Lys Val Ala Leu Gly Lys Thr Leu Gly Glu
                530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
                580                 585                 590

Asp His Pro Asn Val Met Arg Leu Ile Gly Val Cys Phe Gln Gly Ser
                595                 600                 605

Glu Arg Glu Ser Phe Pro Ala Pro Val Val Ile Leu Pro Phe Met Lys
610                 615                 620
```

-continued

```
His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890
```

<210> SEQ ID NO 3
<211> LENGTH: 885
<212> TYPE: PRT
<213> ORGANISM: Homo sapiens
<220> FEATURE:
<221> NAME/KEY: misc_feature
<223> OTHER INFORMATION: Human Axl isoform 2

<400> SEQUENCE: 3

```
Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95
```

```
Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
            245                 250                 255

His Cys Thr Leu Gln Ala Val Leu Ser Asp Asp Gly Met Gly Ile Gln
        260                 265                 270

Ala Gly Glu Pro Asp Pro Pro Glu Glu Pro Leu Thr Ser Gln Ala Ser
            275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
            325                 330                 335

Pro Glu Asn Ile Ser Ala Thr Arg Asn Gly Ser Gln Ala Phe Val His
        340                 345                 350

Trp Gln Glu Pro Arg Ala Pro Leu Gln Gly Thr Leu Leu Gly Tyr Arg
            355                 360                 365

Leu Ala Tyr Gln Gly Gln Asp Thr Pro Glu Val Leu Met Asp Ile Gly
370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
            405                 410                 415

Trp Ser Leu Pro Val Pro Leu Glu Ala Trp Arg Pro Val Lys Glu Pro
        420                 425                 430

Ser Thr Pro Ala Phe Ser Trp Pro Trp Trp Tyr Val Leu Leu Gly Ala
            435                 440                 445

Val Val Ala Ala Ala Cys Val Leu Ile Leu Ala Leu Phe Leu Val His
        450                 455                 460

Arg Arg Lys Lys Glu Thr Arg Tyr Gly Glu Val Phe Glu Pro Thr Val
465                 470                 475                 480

Glu Arg Gly Glu Leu Val Val Arg Tyr Arg Val Arg Lys Ser Tyr Ser
            485                 490                 495

Arg Arg Thr Thr Glu Ala Thr Leu Asn Ser Leu Gly Ile Ser Glu Glu
        500                 505                 510
```

Leu Lys Glu Lys Leu Arg Asp Val Met Val Asp Arg His Lys Val Ala
515                 520                 525

Leu Gly Lys Thr Leu Gly Glu Gly Phe Gly Ala Val Met Glu Gly
530                 535                 540

Gln Leu Asn Gln Asp Asp Ser Ile Leu Lys Val Ala Val Lys Thr Met
545                 550                 555                 560

Lys Ile Ala Ile Cys Thr Arg Ser Glu Leu Glu Asp Phe Leu Ser Glu
                565                 570                 575

Ala Val Cys Met Lys Glu Phe Asp His Pro Asn Val Met Arg Leu Ile
            580                 585                 590

Gly Val Cys Phe Gln Gly Ser Glu Arg Glu Ser Phe Pro Ala Pro Val
        595                 600                 605

Val Ile Leu Pro Phe Met Lys His Gly Asp Leu His Ser Phe Leu Leu
    610                 615                 620

Tyr Ser Arg Leu Gly Asp Gln Pro Val Tyr Leu Pro Thr Gln Met Leu
625                 630                 635                 640

Val Lys Phe Met Ala Asp Ile Ala Ser Gly Met Glu Tyr Leu Ser Thr
                645                 650                 655

Lys Arg Phe Ile His Arg Asp Leu Ala Ala Arg Asn Cys Met Leu Asn
            660                 665                 670

Glu Asn Met Ser Val Cys Val Ala Asp Phe Gly Leu Ser Lys Lys Ile
        675                 680                 685

Tyr Asn Gly Asp Tyr Tyr Arg Gln Gly Arg Ile Ala Lys Met Pro Val
    690                 695                 700

Lys Trp Ile Ala Ile Glu Ser Leu Ala Asp Arg Val Tyr Thr Ser Lys
705                 710                 715                 720

Ser Asp Val Trp Ser Phe Gly Val Thr Met Trp Glu Ile Ala Thr Arg
                725                 730                 735

Gly Gln Thr Pro Tyr Pro Gly Val Glu Asn Ser Glu Ile Tyr Asp Tyr
            740                 745                 750

Leu Arg Gln Gly Asn Arg Leu Lys Gln Pro Ala Asp Cys Leu Asp Gly
        755                 760                 765

Leu Tyr Ala Leu Met Ser Arg Cys Trp Glu Leu Asn Pro Gln Asp Arg
    770                 775                 780

Pro Ser Phe Thr Glu Leu Arg Glu Asp Leu Glu Asn Thr Leu Lys Ala
785                 790                 795                 800

Leu Pro Pro Ala Gln Glu Pro Asp Glu Ile Leu Tyr Val Asn Met Asp
                805                 810                 815

Glu Gly Gly Gly Tyr Pro Glu Pro Pro Gly Ala Ala Gly Gly Ala Asp
            820                 825                 830

Pro Pro Thr Gln Pro Asp Pro Lys Asp Ser Cys Ser Cys Leu Thr Ala
        835                 840                 845

Ala Glu Val His Pro Ala Gly Arg Tyr Val Leu Cys Pro Ser Thr Thr
    850                 855                 860

Pro Ser Pro Ala Gln Pro Ala Asp Arg Gly Ser Pro Ala Ala Pro Gly
865                 870                 875                 880

Gln Glu Asp Gly Ala
            885

<210> SEQ ID NO 4
<211> LENGTH: 231
<212> TYPE: PRT
<213> ORGANISM: Homo sapiens

```
<220> FEATURE:
<221> NAME/KEY: misc_feature
<223> OTHER INFORMATION: Human Fc p100-k330

<400> SEQUENCE: 4

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

SARS-COV-2 (COVID-19) SPIKE-AXL BINDING ASSAY

CROSS-REFERENCE TO RELATED APPLICATIONS

This application claims priority to U.S. Provisional Patent Application Ser. No. 63/142,266 entitled "SARS-CoV-2 (COVID-19) SPIKE-AXL BINDING ASSAY" filed on Jan. 27, 2021, the entirety of which is hereby incorporated by reference.

TECHNICAL FIELD

The present disclosure is generally related to methods of detecting specific binding between SARS-CoV-2 spike protein and tyrosine-protein kinase receptor UFO (AXL). The present disclosure is also generally related to kits for the performance of the methods of the disclosure.

SEQUENCE LISTING

This application contains a sequence listing filed in electronic form as an ASCII.txt file entitled "2208031140_ST25" created on Jun. 10, 2021. The content of the sequence listing is incorporated herein in its entirety.

BACKGROUND

The coronavirus disease 2019 (COVID-19) pandemic remains an urgent global public health concern, with at least 76 million cases reported and over 1.6 million deaths worldwide as of December 2020. Although several vaccines are under clinical trials, the number of infections and fatalities will continue to rise for the foreseeable future resulting in a catastrophic impact on societal health and economic development. Numerous medications have been tested for efficacy against COVID-19, notably Remdesivir®, among others, but few of these therapies have demonstrated robust efficacy in clinical trials. Therefore, hospital care of COVID-19 patients will become commonplace world-wide and treating complications such as cytokine storm and organ failure in severe cases will necessitate increase investigations into the efficacy of new treatments.

The causative agent of COVID-19, severe acute respiratory syndrome coronavirus 2 (SARS-CoV-2) is a member of the Coronaviridae family of viruses that are known to cause respiratory, hepatic, enteric, and neurologic diseases in mammals. Before 2002, coronaviruses were known only as minor human pathogens, contributing to about 15-25% of common colds However, the emergence of a severe outbreak of SARS in 2002 caused by the novel coronavirus SARS-CoV propelled public health vigilance for diseases caused by corona viruses. To date, there are seven known coronavirus of zoonotic origin that can cause human illness, with the coronaviruses MERS-CoV, SARS-CoV, and SARS-CoV-2 identified as being causal of severe acute respiratory syndrome.

The coronavirus disease 2019 (COVID-19) is caused by the SARS-CoV-2 virus. A critical step of infection is when the virus enters human host cells, which is enabled by the interaction between the SARS-CoV-2 Spike (S) protein's receptor binding domain (RBD) on the surface of the viral particle and receptors on the surface of human cells. Thus, the identification of small molecules, antibodies such as virus neutralizing antibodies, or other biological molecules that interfere with the formation of the S-receptor complex could help to develop drugs to prevent or treat COVID-19.

SUMMARY

One aspect of the disclosure, therefore, encompasses embodiments of a method of detecting an inhibitor of binding between the spike protein (S1F) of the SARS-CoV-2 (Covid-19) virus and tyrosine-protein kinase receptor UFO (AXL), the method comprising the steps: (a) contacting a glycosylated S1F polypeptide with a mammalian AXL polypeptide, wherein the S1F polypeptide is bound to the wells of a microtiter plate, can be a recombinant glycosylated polypeptide expressed from a mammalian cell expression system, and can have the amino acid sequence SEQ ID NO: 1, and the AXL fragment has the amino acid sequence SEQ ID NO: 2 or 3; (b) contacting the well-bound glycosylated S1F polypeptide with the AXL fragment, and then incubating the wells for a period that allows the well-bound glycosylated S1F spike protein to form a well-bound complex with the AXL fragment delivered thereto; (c) washing the wells of unbound polypeptides; (d) delivering to the wells from step (c) a detectably labeled anti-AXL-specific antibody; (e) incubating the wells for a period to allow the anti-AXL-specific antibody to bind to the well-bound complex formed in step (b); (f) washing the wells of unbound polypeptides; (g) detecting a signal generated by the label on the anti-AXL-specific antibody bound to the well-bound complex, thereby detecting binding of the S1F polypeptide to the AXL fragment; (h) repeating steps (a)-(g), wherein in step (a) a suspected inhibitor of S1F-AXL binding can be added to the wells of the microtiter plate, wherein the suspected inhibitor can be either-(1) a small molecule, a Covid-19 virus-specific antibody, or a peptide, or (2) a biological sample suspected of comprising at least one of a SARS-CoV-2 (Covid-19) virus or a Covid-19 virus-specific antibody that inhibits binding of the S1F to AXL; and (i) measuring the difference between the signals from the detectable label in the absence and presence of the suspected S1F-AXL binding inhibitor, wherein lower signal intensity generated in the presence of the suspected inhibitor compared to the signal intensity in the absence of the suspected inhibitor indicates that the suspected inhibitor is an inhibitor or comprises an inhibitor of S1F-AXL binding and the degree of the signal intensity reduction further indicates the magnitude of the inhibition.

In some embodiments of this aspect of the disclosure the label can be horse radish peroxidase (HRP).

In some embodiments of this aspect of the disclosure the S1F protein and the mammalian AXL polypeptide are both glycosylated.

Another aspect of the disclosure encompasses embodiments A method of detecting an inhibitor of binding between the spike protein (S1F) of the SARS-CoV-2 (Covid-19) virus and tyrosine-protein kinase receptor UFO (AXL), the method comprising the steps: (a) contacting a glycosylated virus spike S1F polypeptide of the SARS-CoV-2 (Covid-19) with a mammalian AXL polypeptide, thereby forming an AXL-S1F complex immobilized on the surfaces of the wells, wherein the AXL polypeptide is bound to the surfaces of wells of a microtiter plate and has the amino acid sequence SEQ ID NO: 2 or 3 and the S1F polypeptide is a recombinant glycosylated polypeptide expressed from a mammalian cell expression system, has the amino acid sequence SEQ ID NO: 1, and has a tag conjugated thereto; (b) washing the wells of unbound polypeptides; (c) delivering to the wells from step (b) a detectably labeled antitag-specific antibody; (d) incubating the wells for a period to allow the anti-tag-specific antibody delivered thereto to bind to the complex formed in step (a); (e) detecting the label on the anti-tag-specific antibody bound to the complex immobilized on the microtiter plate, thereby detecting binding of the S1F to the immobilized AXL; (f) repeating steps (a)-(e), wherein in step (a) a suspected inhibitor of the binding of the S1F to AXL is added to the wells of the microtiter plate, wherein the suspected inhibitor is either (1) a small molecule, a Covid-19 virus-specific antibody, or a peptide, or (2) a biological sample suspected of comprising at least one of a SARS-CoV-2 (Covid-19) virus or a Covid-19 virus-specific antibody that inhibits binding of the S1F to AXL; and (g) measuring the difference between a signal from the detectable label in the absence and presence of the suspected inhibitor of binding of the S1F polypeptide to the AXL polypeptide, wherein a reduction in the intensity of the signal generated in the presence of the suspected inhibitor indicates that the suspected inhibitor is an inhibitor or comprises an inhibitor of S1F-AXL binding and the degree of the reduction indicates the magnitude of the inhibition.

In some embodiments of this aspect of the disclosure the tag conjugated to the S1F polypeptide is an immunoglobulin G (IgG) Fc region and the anti-tag-specific antibody is an anti-IgG Fc-specific antibody.

In some embodiments of this aspect of the disclosure the label can be horse radish peroxidase (HRP).

In some embodiments of this aspect of the disclosure the S1F polypeptide and the mammalian AXL polypeptide are both glycosylated.

Yet another aspect of the disclosure encompasses embodiments of a kit that comprises at least one microtiter plate comprising a plurality of wells, wherein an AXL polypeptide or a glycosylated Covid-19 virus S1F polypeptide is immobilized on the surfaces of the wells, the kit further comprising vessels that contain a wash buffer, an assay diluent, at least one of a glycosylated S1F polypeptide having a tag conjugated thereto and an AXL polypeptide, an anti-AXL polypeptide detection antibody when the S1F polypeptide is immobilized on the surfaces of the wells or an anti-tag antibody when the AXL polypeptide is immobilized on the surfaces of the wells, a TMB One-Step Substrate Reagent comprising 3,3',5,5'-tetramethylbenzidine (TMB) in a buffer, and a reaction stop solution comprising about 0.2M sulfuric acid, and instructions for the use of the kit to assay the binding of the AXL polypeptide to the S1 FF polypeptide in the absence and presence of a compound or a biological sample suspected of inhibiting said binding.

In some embodiments of this aspect of the disclosure the tag conjugated to the S1F polypeptide is an immunoglobulin G (IgG) Fc region and the anti-tag-specific antibody is an anti-IgG Fc-specific antibody.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 4 schematically shows an alternative embodiment of the assay method of the disclosure wherein a mammalian cell-expressed (glycosylated) spike S1F polypeptide coats the surfaces of the wells of a microtiter plate and AXL binds to the surface-immobilized spike S1F. An anti-AXL antibody is bound to the AXL and detected with an anti-Fc antibody conjugated to a detectable label.

Figure 6A:
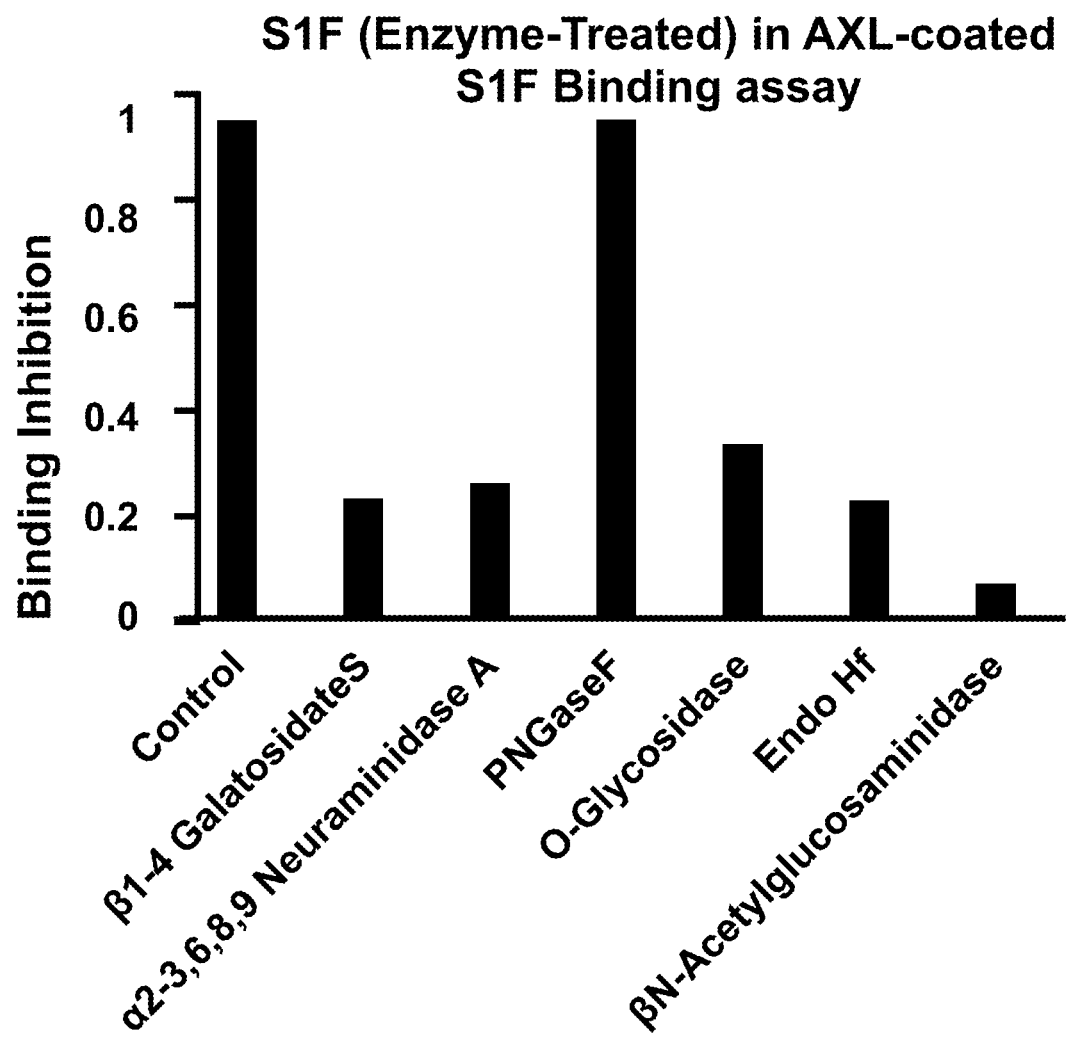

FIG. 6A illustrates the effect on the binding of AXL and S1F proteins of treating glycosylated S1F with different glycosidases.

FIG. 7 illustrates the effect of deglycosylated S1F in an AXL-S1F Binding Assay. Microtiter plate wells were coated with AXL protein (60 ng/ml) and S1F protein (125 ng/ml) (glycosylated or deglycosylated) was added and incubated 1.5 hr followed by the primary antibody added at 1:2000 (1 mg/ml) and mouse IgG secondary was added at 1:3000. The $OD_{450}$ was measured after addition of TMB followed by stop solution.

FIG. 8 illustrates an AXL-S1F binding assay. AXL protein (154-AL, R&D Systems, Minnesota) was coated (62.5 ng/ml). S1F protein was added at different concentrations and incubated 1.5 hr followed by the primary antibody added at 1:2000 (1 mg/ml) and mouse IgG secondary added at 1:5000. The $OD_{450}$ was measured after the addition of TMB followed by stop solution FIG. 9 illustrates the effect of deglycosylating AXL on S1F-AXL binding. Microtiter wells were coated with S1F protein (125 ng/ml). Chimeric AXL-Fc-H6 protein (Cat No. 154-AL (R&D Systems, Minnesota) was added (glycosylated or deglycosylated) at different concentrations and incubated 1.5 hr followed by the primary antibody (mAb 154 from R&D Systems, Minnesota) at 1:2000 (1 mg/ml) and mouse IgG secondary was added at 1:5000. The $OD_{450}$ was measured after the addition of TMB followed by stop solution.

DETAILED DESCRIPTION

Figure 1:
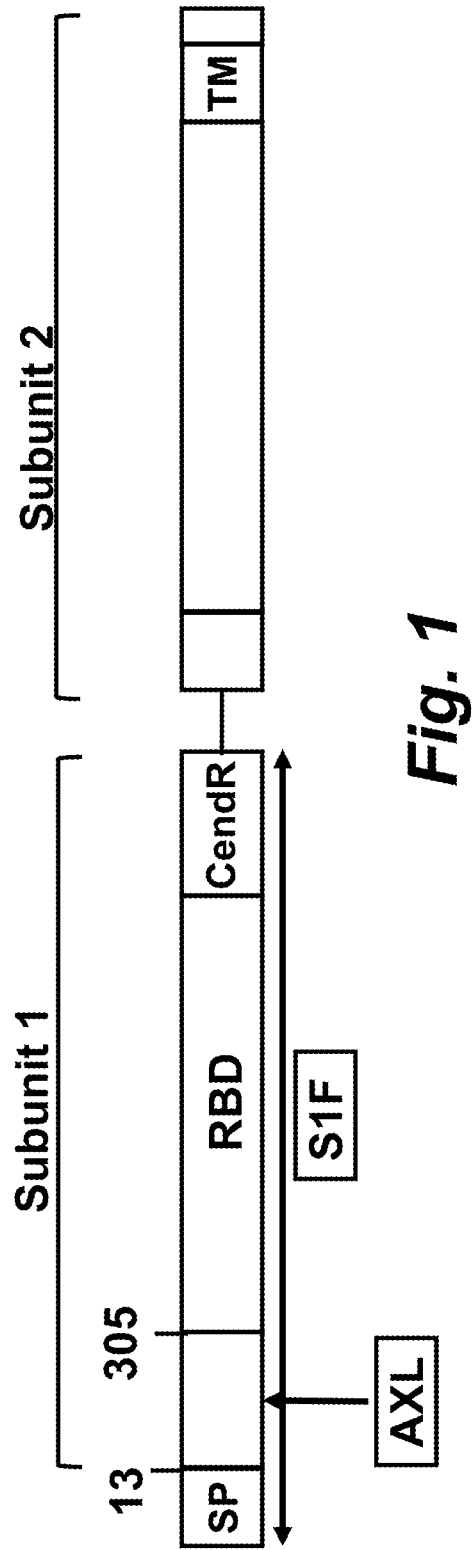
FIG. 1 schematically illustrates the subunit and domain composition of the SARS-CoV-2 (Covid-19) virus Spike protein. The S1F polypeptide (SEQ ID NO: 1) is shown as S1. The N-terminal domain (NTB) (amino acid positions 13-305) to which the AXL polypeptide binds is shown.
Figure 2:
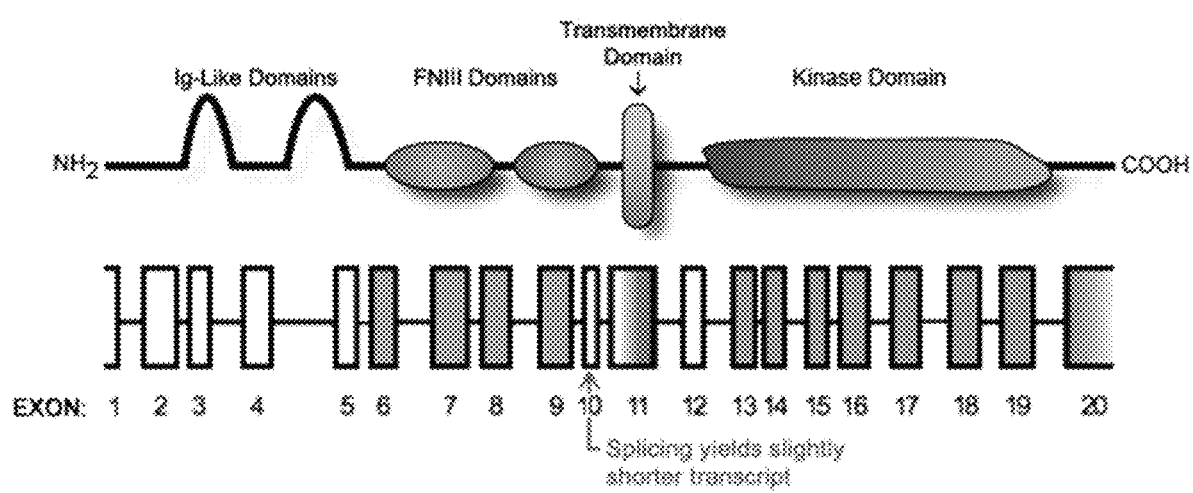
FIG. 2 illustrates the structure of the AXL gene (bottom) roughly aligned with its corresponding functional protein domains (top). Boxes represent individual exons.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Abbreviations

ELISA, Enzyme Linked Immunoglobulin Sandwich Assay; TMB, 3,3,5,5'-tetramethylbenzidine; SARS-CoV-2, Severe Acute Respiratory Syndrome Coronavirus 2; COVID-19, coronavirus disease 2019; RBD receptor binding domain.

Definitions

The term "specific binding" as used herein refers to the specific recognition of one molecule for a different molecule, compared to substantially less recognition of other molecules. Generally, the molecules have areas on their surfaces or in cavities giving rise to specific recognition between the two molecules. Exemplary of specific binding are antibody-antigen interactions.

The term "antibody" as used herein refers to an immunoglobulin which specifically binds to and is thereby defined as complementary with a particular spatial and polar organization of another molecule. The antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, IgY, etc. Fragments thereof may include Fab, Fv and F(ab')2, Fab', scFv, and the like. In addition, aggregates, polymers, and conjugates of immunoglobulins or their fragments can be used where appropriate so long as binding affinity for a particular molecule is maintained.

Antibodies may be derived from any source, including, but not limited to, murine spp., rat, rabbit, chicken, human, or any other origin (including humanized antibodies). Techniques for the generation of antibodies that can specifically recognize and bind to are known in the art.

The term "antigen" as used herein refers to any entity that binds to an antibody and induces at least one shared conformational epitope on the antibody. Antigens can be proteins, peptides, antibodies, small molecules, lipid, carbohydrates, nucleic acid, and allergens. An antigen may be in its pure form or in a sample in which the antigen is mixed with other components.

The term "Severe Acute Respiratory Syndrome Coronavirus 2 (SARS-CoV-2)" as used herein refers to the strain of coronavirus that causes coronavirus disease 2019 (COVID-19), the respiratory illness responsible for the COVID-19 pandemic. Colloquially known as simply the coronavirus, it was previously referred to by its provisional name, 2019 novel coronavirus (2019-nCoV), and has also been called human coronavirus 2019 (HCoV-19 or hCoV-19). SARS-CoV-2 is a Baltimore class IV positive-sense single-stranded RNA virus that is contagious in humans. It is the successor to SARS-CoV-1, the strain that caused the 2002-2004 SARS outbreak.

Each SARS-CoV-2 virion is 50-200 nm in diameter. Like other coronaviruses, SARS-CoV-2 has four structural proteins, known as the S (spike), E (envelope), M (membrane), and N (nucleocapsid) proteins; the N protein holds the RNA genome, and the S, E, and M proteins together create the viral envelope. The spike protein, which has been imaged at the atomic level is responsible for allowing the virus to attach to and fuse with the membrane of a host cell; specifically, its S1 subunit catalyzes attachment, the S2 subunit fusion.

SARS-CoV-2 has sufficient affinity to the receptor angiotensin converting enzyme 2 (ACE2) on human cells to use them as a mechanism of cell entry. Studies have shown that SARS-CoV-2 has a higher affinity to human ACE2 than the original SARS virus strain.

Initial spike protein priming by transmembrane protease, serine 2 (TMPRSS2) is essential for entry of SARS-CoV-2. After a SARS-CoV-2 virion attaches to a target cell, the cell's protease TMPRSS2 cuts open the spike protein of the virus, exposing a fusion peptide in the S2 subunit, and the host receptor ACE2. After fusion, an endosome forms around the virion, separating it from the rest of the host cell. The virion escapes when the pH of the endosome drops or when cathepsin, a host cysteine protease, cleaves it. The virion then releases RNA into the cell and forces the cell to produce and disseminate copies of the virus, which infect more cells.

The terms "binding" as used herein refers to the non-covalent interactions of the type between a first polypeptide molecule and a second polypeptide. The strength, or affinity of binding interactions can be expressed in terms of the dissociation constant ($K_d$) of the interaction, wherein a smaller $K_d$ represents a greater affinity. Binding properties of selected polypeptides can be quantified using methods well known in the art. One such method entails measuring the rate of complex formation and dissociation of the two interacting polypeptides, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$.

The term "tag" as used herein refers to a moiety conjugated to a molecule such as a peptide or a polypeptide that it is desirable to label but does not necessarily have the label attached. A tag can allow a label or labelled moiety to specifically bind to the tag. A tag may be a small molecule to which the labeled moiety can bind, a larger molecule such as a peptide, e.g. a hexa-histidine chain, a polypeptide or combination of polypeptide chains such as, but not limited to, an Fc region of an antibody, any of which may be selectively bound by a suitably selected labeled moiety such as, but not limited to an anti-Fc region antibody.

By "detectably labeled" is meant that a polypeptide or a fragment thereof, contains a moiety that elicits a physical or chemical response, such as a fluorophore or dye, and which can be observed or detected by the naked eye or by means of instrumentation such as, without limitation, colorimeters, UV spectrophotometers and the like.

The term "detectable moiety" as used herein refers to a label molecule (isotopic or non-isotopic). Thus, "detectable moiety" is used synonymously with "label molecule". Label molecules, known to those skilled in the art as being useful for detection, include chemiluminescent or fluorescent molecules. The protocol for such incorporation may vary depending upon the fluorescent molecule used. Such protocols are known in the art for the respective fluorescent molecule.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far-red part of the spectrum; quantum yield is 0.28. FW=792. Suitable fluorophores(chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.), HILYTE™ Fluors (AnaSpec), and DYLITE™ Fluors (Pierce, Inc).

The term "fluorophore" as used herein refers to any reporter group whose presence can be detected by its light emitting properties.

The term "immobilized on a solid support" as used herein refers to a polypeptide attached to a substrate at a particular location so that it may be subjected to washing or other physical or chemical manipulation without being dislodged. A number of solid supports and immobilizing methods are known in the art, and may be used in the methods of this disclosure.

The term "surface" as used herein refers to a solid support such as the surface of the bottom of a well of a microtiter plate, which are particularly useful for in vitro assays. Such solid supports might be porous or nonporous, planar or nonplanar and include, but are not limited to, glass, cellulose, polyacrylamide, nylon, polystyrene, polyvinyl chloride or polypropylene supports. As another example, the polypeptides of the invention can usefully be attached to the surface of a microtiter plate for ELISA.

The terms "expressed" and "expression" as used herein refer to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, an amino acid sequence or a portion thereof.

The term "fragment" of a protein or nucleic acid as used herein refers to any portion of the amino acid sequence. That in the context of the present disclosure retains the ability of an S1F polypeptide to bind to a AXL polypeptide, and vice versa.

The term "immunoglobulin" as used herein refers to a class of proteins that exhibit antibody activity and bind to other molecules (e.g., antigens and certain cell-surface receptors) with a high degree of specificity. Immunoglobulins can be divided into five classes: IgM, IgG, IgA, IgD, and IgE. IgG is the most abundant antibody class in the body and assumes a twisted "Y" shape configuration. With the exception of the IgMs, immunoglobulins are composed of four peptide chains that are linked by intrachain and interchain disulfide bonds. IgGs are composed of two polypeptide heavy chains (H chains) and two polypeptide light chains (L chains) that are coupled by non-covalent disulfide bonds.

The light and heavy chains of immunoglobulin molecules are composed of constant regions and variable regions. For example, the light chains of an IgG1 molecule each contain a variable domain ($V_L$) and a constant domain ($C_L$). The heavy chains each have four domains: an amino terminal variable domain ($V_H$), followed by three constant domains ($C_H1$, $C_H2$, and the carboxy terminal $C_H3$). A hinge region corresponds to a flexible junction between the $C_H1$ and $C_H2$ domains. Papain digestion of an intact IgG molecule results in proteolytic cleavage at the hinge and produces an Fc fragment that contains the $C_H2$ and $C_H3$ domains, as well as two identical Fab fragments that each contain a $C_H1$ $C_L$, $V_H$, and $V_L$ domain. The Fc fragment has complement- and tissue-binding activity. The Fab fragments have antigen-binding activity Immunoglobulin molecules can interact with other polypeptides through a cleft within the $C_H2$-$C_H3$ domain. This "$C_H2$-$C_H3$ cleft" typically includes the amino acids at positions 251-255 within the $C_H2$ domain and the amino acids at positions 424-436 within the $C_H3$ domain. As used herein, numbering is with respect to an intact IgG molecule as in Kabat et al. (Sequences of Proteins of Immunological Interest, 5th ed., Public Health Service, U.S. Department of Health and Human Services, Bethesda, Md.). The corresponding amino acids in other immunoglobulin classes can be readily determined by those of ordinary skill in the art.

The Fc region can bind to a number of effector molecules and other proteins, including the cellular Fe Receptor that provides a link between the humoral immune response and cell-mediated effector systems (Hamano et al., (2000) *J. Immunol.* 164: 6113-6119; Coxon et al., (2001) *Immunity* 14: 693-704; Fossati et al., (2001) *Eur. J. Clin. Invest.* 31: 821-831). The Fcγ receptors are specific for IgG molecules, and include FcγRI, FcγRIIa, FcγRIIb, and FcγRIII. These isotypes bind with differing affinities to monomeric and immune-complexed IgG.

The term "polypeptide" includes proteins and fragments thereof. Polypeptides are disclosed herein as amino acid residue sequences.

The term "recombinant" as used herein, and referring to a nucleic acid molecule, means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide The term "monoclonal antibody" or "mAb" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "small molecule" as used herein refers to an organic compound, including an organometallic compound, of a molecular weight less than about 2 kDa, that is not a polynucleotide, a polypeptide, a polysaccharide, or a synthetic polymer composed of a plurality of repeating units.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric. Use of "polypeptide" herein is intended to encompass polypeptide and fragments and variants (including fragments of variants) thereof, unless otherwise stated.

The term "sample," as used herein, is used in its broadest sense. A "biological sample," as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

The term "control" refers to a composition known to not contain analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

The terms "specific" and "specificity" as used herein are in the context of an interaction between members of a specific binding pair (e.g., an antigen (or fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to analyte (or a fragment thereof) and not bind specifically to other entities.

The term "glycosylation" as used herein refers to the attachment of carbohydrate moieties and chains to a protein or polypeptide. Glycosylation of polypeptides is typically either "N-linked" or "O-linked. "N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. "O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

The term "AXL" as used herein refers to tyrosine-protein kinase receptor UFO (also designated as AXL, AZF, AZFA, SP3, AZF1, ARK, JTK11, Tyro7, UFO, AXL receptor tyrosine kinase), an enzyme that in humans is encoded by the AXL gene. The protein AXL is an 894 amino acid protein with a molecular weight of between about 104 to about 140 kDa that is part of the subfamily of mammalian TAM Receptor Tyrosine Kinases (RTKs). The molecular weight is variable due to potential differences in glycosylation of the protein. The AXL protein consists of two extracellular immunoglobulin-like (Ig-like) domains on the N-terminal end of the protein, two membrane-proximal extracellular fibronectin type III (FNIII) domains, a transmembrane domain and an intracellular kinase domain. AXL is activated upon binding of its ligand Gas6, by ligand-independent homophilic interactions between AXL extracellular domains, by autophosphorylation in presence of reactive oxygen species or by transactivation through EGFR, and is aberrantly expressed in several tumor types. In humans, the AXL protein is encoded by a nucleic acid sequence encoding the amino acid sequence shown in SEQ ID NO: 2 (human AXL protein: Swissprot P30530).

There are two transcript variants of AXL. In humans, transcript variant 1 encodes the full-length AXL isoform (isoform 1), and transcript variant 2 lacks exon 10, resulting in a protein (isoform 2) lacking an internal 9 amino acids, but which is otherwise the same as the full length protein encoded by transcript variant 1. The amino acid sequence of human AXL isoform 1 is according to SEQ ID NO: 2. The amino acid sequence of human AXL isoform 2 is according to SEQ ID NO: 3.

The extracellular domain of human AXL spans amino acid positions from about 1 to about 445, and contains two Ig domains and two FNIII domains. The first Ig domain, Ig1, includes from about position 33 to about position 137. The second Ig domain, Ig2, includes from about position 139 to about position 222. The FNIIIa domain includes from about position 225 to about position 328. The FNIII(b) domain includes from about position 337 to about position 418.

The term "Spike (S) protein" as used herein refers to a large glycosylated transmembrane protein ranging from about 1162 to 1452 amino acid residues. Monomers of the S protein, prior to glycosylation, are 128-160 kDa, but molecular masses of the glycosylated forms of the full-length monomer are 150-200 kDa. Following translation, the proteins fold into a metastable prefusion form and assemble into a homotrimer forming the coronavirus distinctive surface spike of crown-like appearance. The S protein is the most outward envelope protein of the coronaviruses. The S glycoprotein plays critical roles in mediating virus attachment to the host cell receptors and facilitating fusion between viral and host cell membranes. In addition, it is the primary determinant of the coronavirus tropism. Changes in the S protein especially in the regions involved in the interactions with entry receptors, may result in altered host, tissue, or cellular tropism of the coronaviruses. The S protein is the main antigen present at the surface of the coronaviruses functioning as a major inducer of host immune responses. During infection, the S protein is the target of the neutralizing antibodies. Therefore, it has been a focus in vaccine design.

The multifunctional S protein can be divided into two functionally distinct subunits: the S1 and S2 subunits (FIG. 1). The global S1 subunit is critical for receptor recognition, while the S2 subunit is important for membrane fusion and for anchoring the S protein into the viral membrane. The S1 subunit consists of two major domains which fold independently, the N-terminal domain (S1-NTD) and the C-terminal domain (S1-CTD). Depending on the virus, one or both of these domains may bind to receptors and function as a receptor-binding domain (RBD). The roles of the S1-CTDs are to bind to protein receptors such as ACE2, APN, and DPP4. Structural studies of SARS-CoV RBD revealed that the RBD contains a core and a motif termed receptor-binding motif (RBM) which is critical for forming contact with receptor.

The term "SARS-CoV-2 S1F" and "S1F as used herein refer to the amino acid sequence having GenBank accession number QHD43416 (SEQ ID NO: 1).

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

DISCUSSION

The present disclosure encompasses embodiments of a variant ELISA-based assay that employs a glycosylated S1F polypeptide derived from the SARS-CoV-2 (Covid-19) virus spike protein and has at least 95% similarity with the amino acid sequence SEQ ID NO: 1. In particular, the glycosylated polypeptide is from the S1 region of the spike protein and may include not just the S1 receptor binding domain (S1RBD) but also the N-terminus of the S protein that has specific binding affinity for a region of A×L-1. AXL assists viral entry into a target cell.

Tyrosine protein kinase receptor UFO (AXL) has been demonstrated to promote SARS-CoV-2 infection by binding to the N-terminus of the S protein (Wang et al., *Cell research* (2021): 1-15). Overexpression of the receptor increased infectivity in cell culture, whereas knocking the receptor out decreased infectivity.

The assays of the disclosure employ the ability of such an S1F polypeptide to specifically bind to AXL and the novel finding that the affinity of the S1F polypeptide for the AXL protein is significantly elevated by the glycosylation of at least the AXK polypeptide and is further enhanced by glycosylation of both the S1F and AXL polypeptides. Accordingly, the assays of the disclosure are in alternative embodiments. In one embodiment, illustrated in FIG. 3, the AXL polypeptide is immobilized on a surface, such as the bottom surface of a well of a microplate known in the art, and is then contacted by a buffered solution of a tagged S1F polypeptide. The complex thus formed in then detected by a labeled anti-tag antibody. In one alternative embodiment the anti-S1F antibody is conjugated to a detectable label such as, but not limited to, a luciferase.

In the alternative it is the spike-S1F polypeptide that is immobilized and contacted with the AXL spike polypeptide fragment that is conjugated to a detectable tag or by a labeled antibody.

A notable feature of the S protein of SARS-CoV-2 is that it is extensively decorated with up to a hundred N-linked glycans, a process that occurs by viral hijacking of the host's glycosylation pathways. Glycosylation of viral structures such as S proteins, contributes to the viruses host immune evasion strategies through the masking antigenic epitopes. Structural data along with glycoproteomics analyses have proposed that extensive glycosylation of the spike protein shields against neutralizing antibodies access (Xiong et al., (2018) *J. Virol.* 92(4): 1-16). Importantly, the glycans on S protein possibly have an unappreciated role in both the stability of S and resultant host cell receptor interactions and cell membrane fusion during entry into the host cell. This gap in the knowledge underscores an exigent need for characterizing the relative influence of SARS-CoV-2 S protein glycosylation in identifying the molecular basis of this interaction with AXL, and the influence of glycans on infectivity.

It has now been found that N-glycosylation of the pike 1, full-length polypeptide (spike S1F) is necessary for in vitro binding to AXL. Likewise, it has been found that N-glycosylation of AXL may also necessary for in vitro binding to spike S1F. These data have now allowed for the development of the assays of the disclosure that provide a sensitive means of detecting and measuring AXL/spike S1F binding. It is possible to adapt this assay for the identification of potential inhibitors of the AXL/spike protein binding that may be advantageous for use as inhibitors of SARS-CoV-2 infection of cells and also to detect antibodies that can inhibit this binding, indicating that a person has been exposed to the virus, as well as identifying antibodies that have therapeutic potential.

Figure 3:
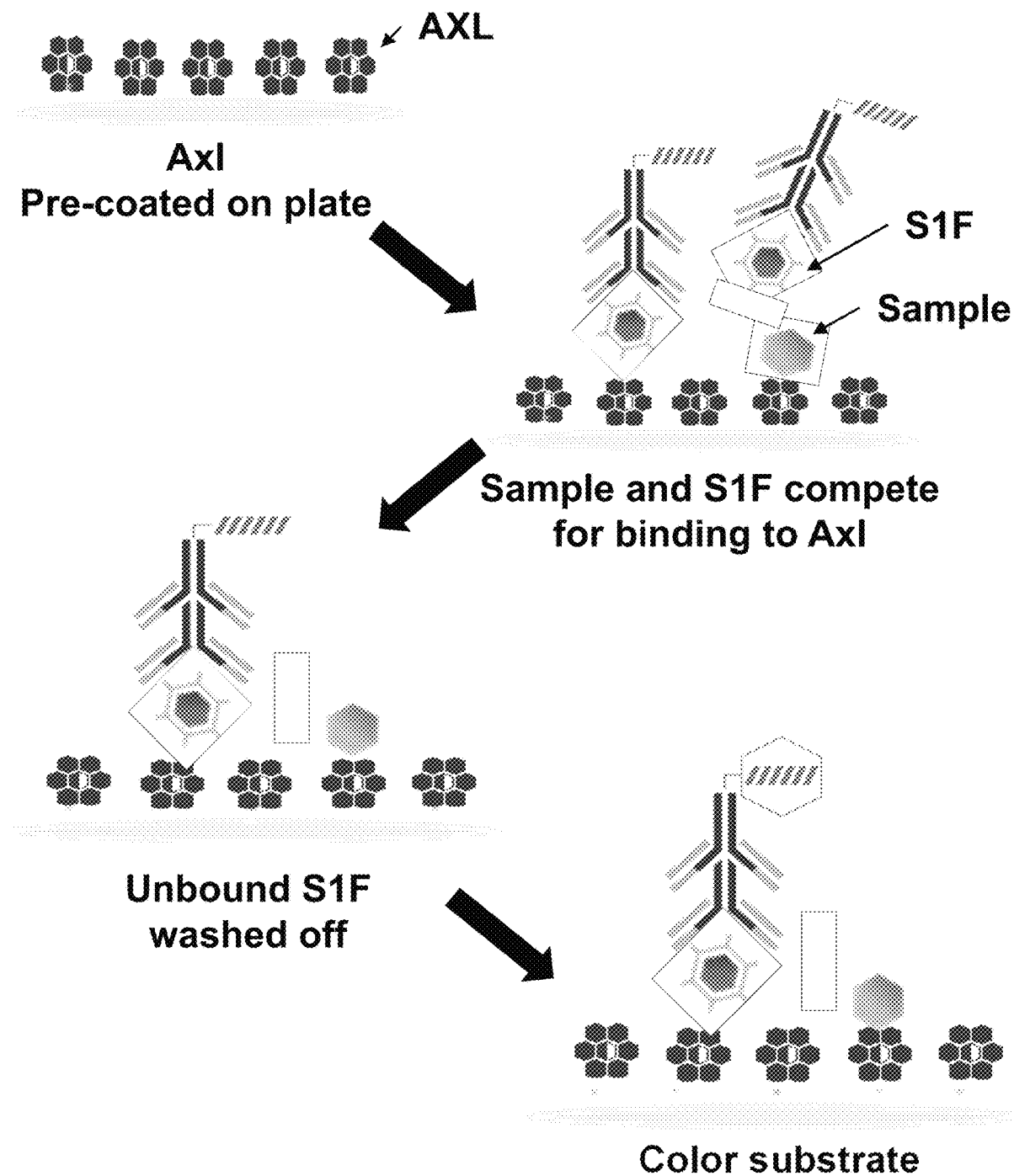
FIG. 3 schematically shows an embodiment of the assay method of the disclosure where the AXL polypeptide coats the surfaces of the wells of a microtiter plate, a mammalian cell-expressed (glycosylated) spike S1F polypeptide tagged with an IgG Fc region binds to the AXL. The bound complex is detected with a mouse anti-spike S1F-specific antibody. After washing away any unbound mouse anti-spike S1F-specific antibody, the remaining mouse anti-spike S1F-specific antibody is detected with an anti-mouse Fc antibody conjugated to a detectable label.
Figure 5:
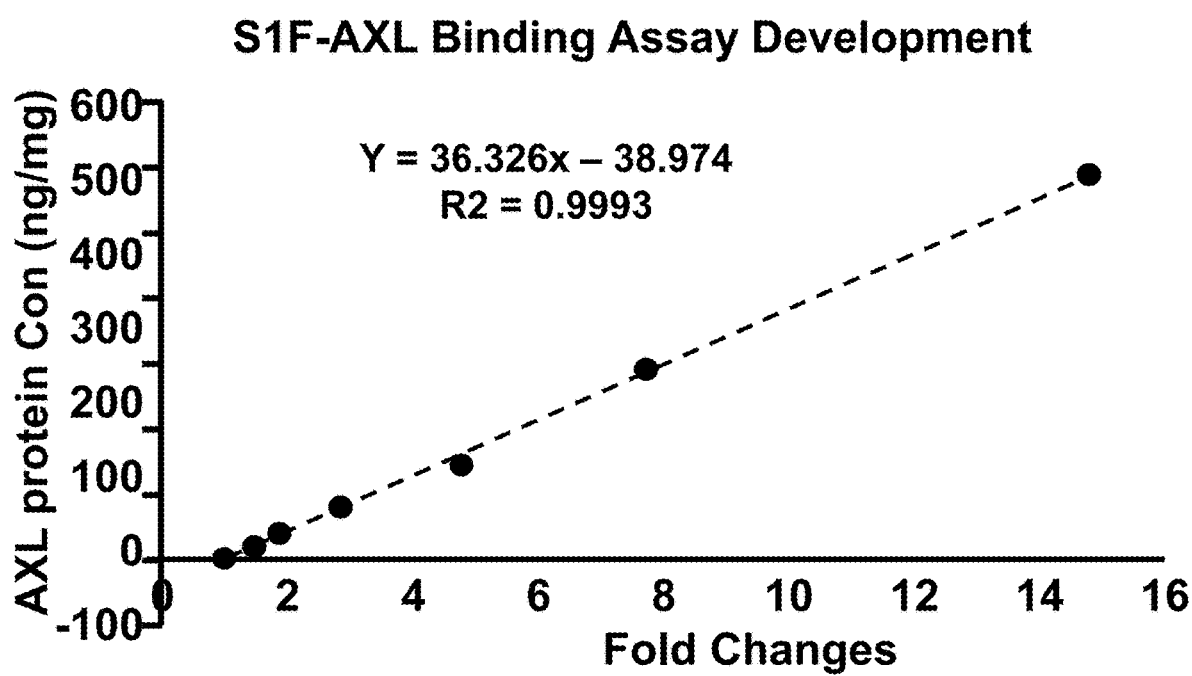
FIG. 5 illustrates immobilized S1F protein (125 ng/ml) and AXL protein (154-AL from R&D) was added at different concentration and incubated 1&½ hr. The primary antibody was added (mAb 154 from R&D) at 1:2000 (1 mg/ml) and mouse IgG secondary antibody was added at 1:5000. The $OD_{450}$ was measured after addition of TMB followed by stop solution.
Figure 6B:
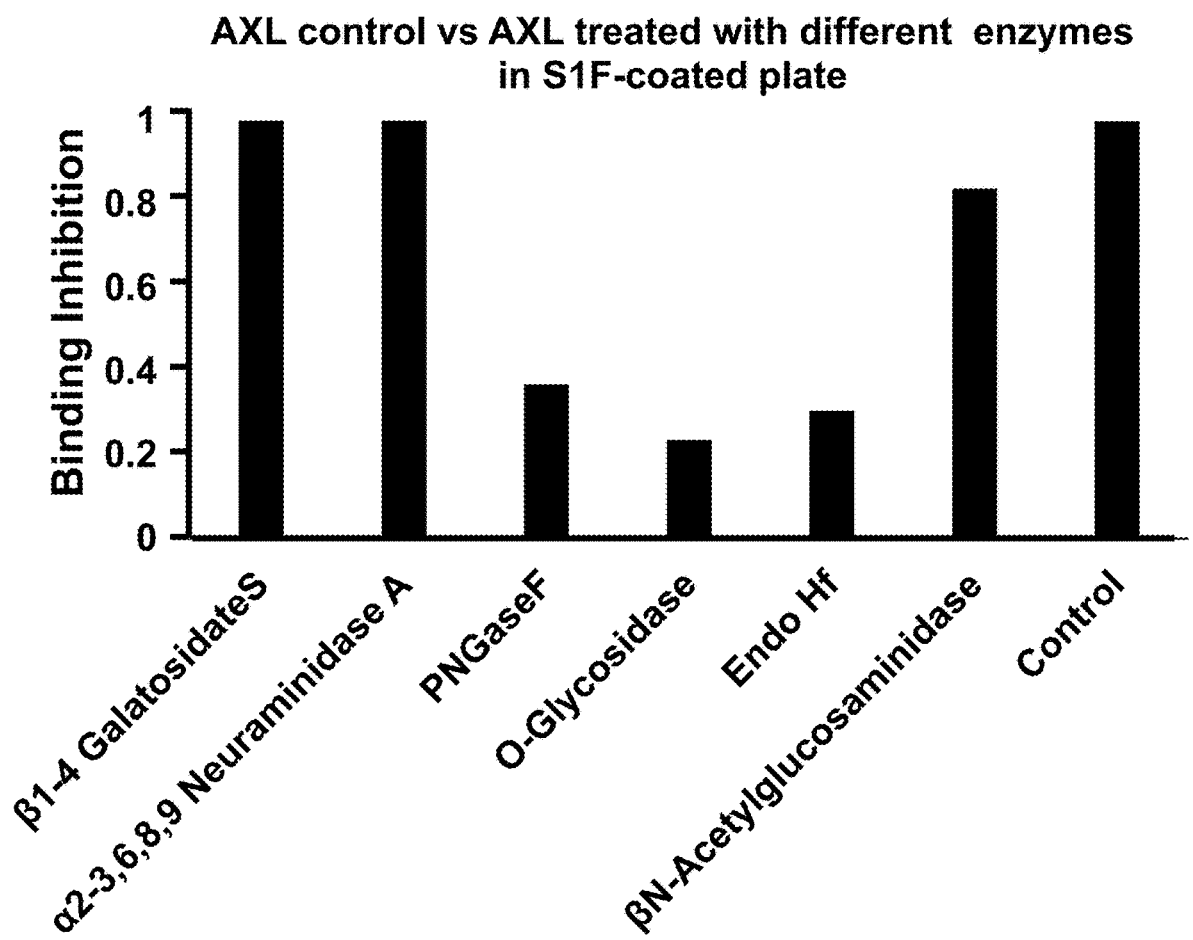
FIG. 6B illustrates the effect on the binding of AXL and S1F proteins of treating glycosylated AXL with different glycosidases.

Unlike with other ELISA-based assays known in the art, the spike S1F polypeptide of the assay is advantageously generated by expression of an encoding nucleic acid by a mammalian (most advantageously human) cell expression system. This results in glycosylation of the expressed S1F polypeptide which surprisingly and significantly increases the affinity of the S1F polypeptide for AXL. Use of the glycosylated form of the S1F, therefore, provides a significant increase in the sensitivity of the assay compared to other known assays, increasing the ability of the assay to detect much smaller amounts or concentrations of the viral protein or its sensitivity to inhibitors then previously reported, and makes possible a more economic use of reagents. Significantly, the glycosylated S1F polypeptide more closely resembles the glycosylated state of intact viral particles produced from an infected cell rather than does an unglycosylated S1F fragment that has been prepared by deglycosylation of a mammalian cell-produced S1F or by a bacterial expression system used for their manufacture, as shown in the data of FIGS. 3 and 4. Similarly, the glycosylation of the AXL polypeptides of the disclosure are required for binding to the S1F polypeptide.

The present disclosure further encompasses embodiments of an assay where the S1F protein fragment, when not immobilized on the surface of microtiter plate wells and, therefore, intended to bind to immobilized AXL polypeptide includes a tag conjugated thereto. In other embodiments, the S1F polypeptide may be immobilized on the wells and the AXL polypeptide is delivered thereto. The complex thus formed by the binding of the two polypeptides may be detected by a detectable anti-AXL antibody or by a labeled anti-tag antibody. Advantageously, this tag can be, but is not limited to, an Fc portion of an immunoglobulin, most advantageously an IgG Fc region (SEQ ID NO: 4, or the like). This Fc tag can then be targeted by an anti-tag antibody, such as an anti-immunoglobulin G (IgG) Fc-specific antibody that has a detectable label attached thereto.

In one embodiment of the assay of the disclosure, the wells of a microtiter plate are coated with a polypeptide derived from a mammalian, and most advantageously a human AXL. An engineered recombinant mammalian cell-expressed S1F polypeptide having an immunoglobulin Fc region tag attached thereto is then added to the coated wells and then incubated for a time sufficient to allow binding of the S1F fragment to the surface immobilized AXL fragment, after which detection of S1F bound to the AXL polypeptide is by the addition of an (HRP)-conjugated anti-immunoglobulin G (IgG) antibody specific for the immunoglobulin Fc region can then be applied to the wells together with 3,3',5,5'-tetramethylbenzidine (TMB) substrate. The HRP-conjugated anti-IgG antibody will bind specifically to the Fc tag polypeptide bound to the surface-immobilized AXL polypeptide, react with the TMB solution, and produce a blue color, the intensity of which is proportional to the amount of bound S1F. The HRP-TMB reaction is halted with the addition of a Stop Solution, resulting in a blue-to-yellow color change. The intensity of the yellow color is then measured at 450 nm.

This method of the disclosure may be advantageously employed to detect, or measure the amount of, the inhibition of the interaction between S1F and AXL by a compound suspected of being an inhibitor, as shown, for example, schematically in FIG. 3. To detect or identify a potential inhibitor a first assay is performed in the absence of the compound suspected of being an inhibitor. A second parallel test is performed, most advantageously simultaneously with the first test, wherein an amount of the compound suspected of being the inhibitor is added to the second test with the S1F polypeptide. A reduction in the intensity of the final yellow color of the second assay compared to the final color in the first assay indicates that the compound inhibits the S1F-AXL binding while the degree of the reduction can indicate the strength of the inhibition. Accordingly, the assays of the disclosure can be useful to identify negative effectors of the binding of S1F polypeptide to AXL that may be useful in a therapeutic or prophylactic treatment for a SARS-CoV-2 (Covid-19) virus infection, or even for use against related coronavirus infections. Potential inhibitors can be, but are not limited to, small molecules and antibodies. Thus, the sample from a patient may be mixed with the polypeptide not originally attached to well surfaces, antibodies in the sample competing with the detection antibody to reduce the detectable signal.

This method is also useful for the detection of the intact spike protein in a biological sample suspected of, for example, containing intact SARS-CoV-2 (Covid-19) virus or the surface antigens thereof. Compared to available means of detecting the Covid-19 spike protein in subjects suspected of being infected with the virus, the assays of the present disclosure are more significantly more sensitive.

In second embodiment of the assay of the disclosure, the wells of a microtiter plate are coated with mammalian cell-expressed S1F polypeptide. A fragment of a mammalian AXL protein (most advantageously a human AXL polypeptide) is then added to the wells. Unbound AXL polypeptide is removed with washing, and an anti-AXL-specific IgG antibody is then applied to the wells. A horse radish peroxidase-labeled (for example) anti-IgG antibody is the added to the wells in the presence of 3,3',5,5'-tetramethylbenzidine (TMB) substrate. The anti-AXL antibody first binds to the AXL polypeptide bound to the surface-immobilized S1F and then binds labeled anti-IgG antibody to react with the TMB solution, producing a blue color that is proportional to the amount of bound AXL. The HRP-TMB reaction is halted with the addition of the Stop Solution, resulting in a blue-to-yellow color change. The intensity of the yellow color is then measured at 450 nm.

In some embodiments, the AXL polypeptide can have a tag attached thereto, such as an immunoglobulin Fc tag. In the methods of such an embodiment, the labeled secondary antibody can be an anti-tag antibody specifically binding to the tag of the AXL bound to the immobile S1F.

The methods of the disclosure may also be readily adapted for use in lateral flow tests to provide a rapid method to detect an antiviral antibody or spike antigen in a sample such as a blood sample, nasal or sinus mucus, and the like. Such tests are less invasive, cheaper, and offer significantly more rapid results than is provided by the "gold-standard" PCR test (detecting whole virus presence). Most preferably, the lateral flow device can have immobilized AXL polypeptide and the flow then encounters the S1F-tag and HRP-anti-tag antibody.

The second variant of the method of the disclosure may also be advantageously employed to detect or measure the amount of the inhibition of the interaction between S1F and AXL by a compound suspected of being an inhibitor. In this case a first assay is performed in the absence of the compound suspected of being an inhibitor. A second test is performed simultaneously with the first test wherein an amount of the compound suspected of being the inhibitor is added to the second test with the AXL polypeptide. A reduction in the intensity of the final yellow color indicates that the compound is an inhibitor of the S1F-AXL binding and the degree of the reduction can indicate the magnitude of the inhibition.

The orientations of the two interacting components of the assay system of the disclosure can equally be used to detect inhibitors of the S1F-AXL interaction. However, the orientation where the AXL polypeptide is immobilized to the surface may also be used for the detection of virus or free spike protein in a sample added to the well with the S1F reagent as well as useful for the detection of inhibitors of S1F-AXL complexing. This embodiment provides a rapid sensitive and selective assay for the detection of intact SARS-CoV-2 (Covid-19) virus particles in a biological sample from a subject suspected of having an infection of the SARS-CoV-2 (Covid-19) virus.

The COVID-19 Spike-AXL binding assay kits of the disclosure provides materials and instructions for the rapid, simple, and sensitive method of the disclosure to characterize the binding affinity of the S1F-AXL complex in the presence of potential inhibitors. The in vitro enzyme-linked immunosorbent assay can measure numerous reagents and conditions simultaneously. For example, this kit can be used for screening inhibitor activity and drugs, vaccine development, and testing potential therapeutic antibodies.

One aspect of the disclosure, therefore, encompasses embodiments a method of detecting an inhibitor of binding between the spike protein (S1F) of the SARS-CoV-2 (Covid-19) virus and tyrosine-protein kinase receptor UFO (AXL), the method comprising the steps: (a) contacting a glycosylated S1F polypeptide with a mammalian AXL polypeptide, wherein the S1F polypeptide is bound to the wells of a microtiter plate, can be a recombinant glycosylated polypeptide expressed from a mammalian cell expression system, and can have the amino acid sequence SEQ ID NO: 1, and the AXL fragment has the amino acid sequence SEQ ID NO: 2 or 3; (b) contacting the well-bound glycosylated S1F polypeptide with the AXL fragment, and then incubating the wells for a period that allows the well-bound glycosylated S1F spike protein to form a well-bound complex with the AXL fragment delivered thereto; (c) washing the wells of unbound polypeptides; (d) delivering to the wells from step (c) a detectably labeled anti-AXL-specific antibody; (e) incubating the wells for a period to allow the anti-AXL-specific antibody to bind to the well-bound complex formed in step (b); (f) washing the wells of unbound polypeptides; (g) detecting a signal generated by the label on the anti-AXL-specific antibody bound to the well-bound complex, thereby detecting binding of the S1F polypeptide to the AXL fragment; (h) repeating steps (a)-(g), wherein in step (a) a suspected inhibitor of S1F-AXL binding can be added to the wells of the microtiter plate, wherein the suspected inhibitor can be either-(1) a small molecule, a Covid-19 virus-specific antibody, or a peptide, or (2) a biological sample suspected of comprising at least one of a SARS-CoV-2 (Covid-19) virus or a Covid-19 virus-specific antibody that inhibits binding of the S1F to AXL; and (i) measuring the difference between the signals from the detectable label in the absence and presence of the suspected S1F-AXL binding inhibitor, wherein lower signal intensity generated in the presence of the suspected inhibitor compared to the signal intensity in the absence of the suspected inhibitor indicates that the suspected inhibitor is an inhibitor or comprises an inhibitor of S1F-AXL binding and the degree of the signal intensity reduction further indicates the magnitude of the inhibition.

In some embodiments of this aspect of the disclosure the label can be horse radish peroxidase (HRP).

In some embodiments of this aspect of the disclosure the S1F protein and the mammalian AXL polypeptide are both glycosylated.

Another aspect of the disclosure encompasses embodiments A method of detecting an inhibitor of binding between the spike protein (S1F) of the SARS-CoV-2 (Covid-19) virus and tyrosine-protein kinase receptor UFO (AXL), the method comprising the steps: (a) contacting a glycosylated virus spike S1F polypeptide of the SARS-CoV-2 (Covid-19) with a mammalian AXL polypeptide, thereby forming an AXL-S1F complex immobilized on the surfaces of the wells, wherein the AXL polypeptide is bound to the surfaces of wells of a microtiter plate and has the amino acid sequence SEQ ID NO: 2 or 3 and the S1F polypeptide is a recombinant glycosylated polypeptide expressed from a mammalian cell expression system, has the amino acid sequence SEQ ID NO: 1, and has a tag conjugated thereto; (b) washing the wells of unbound polypeptides; (c) delivering to the wells from step (b) a detectably labeled anti-tag-specific antibody; (d) incubating the wells for a period to allow the anti-tag-specific antibody delivered thereto to bind to the complex formed in step (a); (e) detecting the label on the anti-tag-specific antibody bound to the complex immobilized on the microtiter plate, thereby detecting binding of the S1F to the immobilized AXL; (f) repeating steps (a)-(e), wherein in step (a) a suspected inhibitor of the binding of the S1F to AXL is added to the wells of the microtiter plate, wherein the suspected inhibitor is either (1) a small molecule, a Covid-19 virus-specific antibody, or a peptide, or (2) a biological sample suspected of comprising at least one of a SARS-CoV-2 (Covid-19) virus or a Covid-19 virus-specific antibody that inhibits binding of the S1F to AXL; and (g) measuring the difference between a signal from the detectable label in the absence and presence of the suspected inhibitor of binding of the S1F polypeptide to the AXL polypeptide, wherein a reduction in the intensity of the signal generated in the presence of the suspected inhibitor indicates that the suspected inhibitor is an inhibitor or comprises an inhibitor of S1F-AXL binding and the degree of the reduction indicates the magnitude of the inhibition.

In some embodiments of this aspect of the disclosure the tag conjugated to the S1F polypeptide is an immunoglobulin G (IgG) Fc region and the anti-tag-specific antibody is an anti-IgG Fc-specific antibody.

In some embodiments of this aspect of the disclosure the label can be horse radish peroxidase (HRP).

In some embodiments of this aspect of the disclosure the S1F polypeptide and the mammalian AXL polypeptide are both glycosylated.

Yet another aspect of the disclosure encompasses embodiments of a kit that comprises at least one microtiter plate comprising a plurality of wells, wherein an AXL polypeptide or a glycosylated Covid-19 virus S1F polypeptide is immobilized on the surfaces of the wells, the kit further comprising vessels that contain a wash buffer, an assay diluent, at least one of a glycosylated S1F polypeptide having a tag conjugated thereto and an AXL polypeptide, an anti-AXL polypeptide detection antibody when the S1F polypeptide is immobilized on the surfaces of the wells or an anti-tag antibody when the AXL polypeptide is immobilized on the surfaces of the wells, a TMB One-Step Substrate Reagent comprising 3,3',5,5'-tetramethylbenzidine (TMB) in a buffer, and a reaction stop solution comprising about 0.2M sulfuric acid, and instructions for the use of the kit to assay the binding of the AXL polypeptide to the S1 FF polypeptide in the absence and presence of a compound or a biological sample suspected of inhibiting said binding.

In some embodiments of this aspect of the disclosure the tag conjugated to the S1F polypeptide is an immunoglobulin G (IgG) Fc region and the anti-tag-specific antibody is an anti-IgG Fc-specific antibody.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

The COVID-19 Spike-AXL binding assay kit of the disclosure is a rapid, simple, and sensitive method to characterize the binding affinity of the S-AXL complex in the presence of potential inhibitors within 5 hours. The assay method is able to qualitatively and quantitatively detect the activity of various possible inhibitor types, including small molecules, peptides, antibodies, and patient serum, that can inhibit spike S1F-AXL binding. For example, this kit and methods can be used to screen inhibitor activity, help develop COVID-10 vaccines, and test potential therapeutic drugs to treat COVID-19.

The COVID-19 Spike-AXL binding assay of the disclosure uses a 96-well plate coated with recombinantly-expressed AXL. The testing reagent-of-choice is then added to the wells in the presence of recombinant human S1F protein. Unbound S1F is removed with washing, and a mouse anti-S1F antibody is added that binds to the S1F component of the S1F-AXL complex. HRP-conjugated anti-mouse IgG is then applied to the wells in the presence of 3,3',5,5'-tetramethylbenzidine (TMB) substrate. The HRP-conjugated anti-mouse IgG antibody binds to the S1F-bound mouse antibody and reacts with the TMB solution to produce a blue color, the intensity of which is proportional to the amount of bound S1F. The HRP-TMB reaction is halted with the addition of the Stop Solution, resulting in a blue-to-yellow color change. The intensity of the yellow color is then measured at 450 nm.

Materials Required:
1. AXL Microplate (Item A)
  96 wells (12 strips×8 wells) coated with recombinant AXL polypeptide.
2. Wash Buffer Concentrate (20×) (Item B)
  25 ml of 20× concentrated solution
3. 5× Assay Diluent (Item E2)
  15 ml of 5× concentrated buffer
  This item is used to dilute the "test reagent" (that is, the potential inhibitor), AXL protein (Item F), detection antibody (Item C) and HRP-conjugated IgG Concentrate (Item D).
4. COVID-19 Spike S1F protein (Item F)
  2 vials of purified human recombinant S1F (1 vial is enough to assay half microplate)
5. Detection Antibody AXL (Item C-1)
  2 vials of mouse anti-AXL antibody (1 vial is enough to assay half microplate)
6. HRP-conjugated anti-mouse IgG (Item D-1)
  25 µl of 1000× concentrated HRP-conjugated anti-goat IgG
7. TMB One-Step Substrate Reagent (Item H)
  12 ml of 3,3',5,5'-tetramethylbenzidine (TMB) in buffered solution
8. Stop Solution (Item I)
  8 ml of 0.2 M sulfuric acid The kit should be stored at 4° C. ad used within 6 months from the date of shipment.

Also Required:
Microplate reader capable of measuring absorbance at 450 nm.
Shaker.
Pipettes capable of accurately delivering 2 l to 1 ml volumes.
Pipettes capable of delivering 1-25 ml volumes for reagent preparation.
Graduated cylinders: 100 ml and 1 liter
Distilled or deionized water.
Tubes to prepare sample dilutions.

Sample Preparation:
Mix "test reagent" (i.e., potential inhibitor) with S1F protein concentrate
Dilute the mixture with 1× Assay Diluent dilute to make a 1× S1F protein working concentration. Each "test reagent" sample should have the same 1× S1F protein concentration.
The optimal dilutions must be determined empirically. For the initial experiment, a serial dilution (e.g., 5-fold to 5000-fold) to determine the optimal amount of test reagent is used.

Serial Dilution Example
Using a 100 mM stock solution of the "test reagent," label and prepare 5 serial dilution tubes labeled: 20 mM, 2 mM, 0.2 mM, 0.02 mM, and 0.002 mM.
Prepare the first serial dilution tube by mixing the following together in the tube labeled "20 mM" for duplicate analyses:
  50 µl of the "test reagent" stock solution
  2.5 µl of S1F protein concentrate (prepared in Part VI, 4)
  197.5 µl 1× Assay Diluent into the first tube labeled "20 mM".
A control should be included to account any effects that the test reagent's buffer may have on the Spike-AXL interaction. If the "test reagent" is in dimethyl sulfoxide (DMSO), for example, a parallel set of tubes should be prepared with 50 µl of DMSO.
Mix thoroughly.
Pipette 225 µl of the 1× S1F protein working solution into the remaining five labeled tubes (2 mM, 0.2 mM, 0.02 mM, 0.002 mM).
Pipette 25 µl from the prepared 20 mM tube into the second serial dilution tube (2 mM). Mix thoroughly.
Repeat step 5 for each serial dilution, using 25 µl of the prior concentration until the final concentration is reached.

Pipette 225 µl of the 1× S1F protein working solution into a separate tube labeled "0 mM." Pipette 25 µl from the 1× Assay Diluent into the tube labeled "0 mM." Mix thoroughly. This will serve as the positive control.

Reagent Preparation

Bring all reagents and samples to room temperature (18-25° C.) before use.

5× Assay Diluent (Item E2) should be diluted 5-fold with deionized or distilled water before use to make a "1× Assay Diluent."

If the Wash Concentrate (20×) (Item B) contains visible crystals, warm to room temperature and mix gently until dissolved. Dilute 20 ml of Wash Buffer Concentrate into deionized or distilled water to yield 400 ml of "1× Wash Buffer.

Briefly spin the S1F protein (Item F) before use.

Add 100 µl of 1× Assay Diluent into the Item F vial to prepare an AXL protein concentrate. Pipette up and down to mix gently.

The amount of 1× Assay Diluent that is added to Item F differs between the two Spike-AXL binding assay kit formats.

The S1F protein concentrate should be diluted 100-fold with 1× Assay Diluent to yield a "1× S1F Working Solution."

Briefly spin the Detection Antibody (Item C-1) before use. Add 100µl of 1× Assay Diluent into the vial to prepare a detection antibody concentrate. Pipette repeatedly to mix gently (the concentrate can be stored at 4° C. for 5 days or at −80° C. for one month). The mouse anti-S1F antibody concentrate should be diluted 55-fold with 1× Assay Diluent and used to yield a "1× Detection Antibody" solution.

Briefly spin the HRP-conjugated anti-mouse IgG (Item D-1) before use. HRP-conjugated anti-mouse IgG concentrate should be diluted 1000-fold with 1× Assay Diluent to yield a "1× HRP-conjugated anti-goat IgG" solution.

Example

Briefly spin the vial to collect contents to the bottom. Add 5 □l of HRP-conjugated anti-mouse IgG concentrate into a tube with 5 mL 1× Assay Diluent, then pipette repeatedly to mix gently to prepare a 1000-fold diluted HRP-conjugated anti-mouse IgG solution. Mix well.

Assay Procedure

Bring all reagents to room temperature (18-25° C.) before use.

Add 100 µl of each sample into an appropriate well.

Cover with plate holder and incubate for 2.5 hours at room temperature or overnight at 4° C. with shaking.

Discard the solution and wash 4 times with 1× Wash Solution. Wash by filling each well with 1× Wash Buffer (300 µl) using a multi-channel pipette or autowasher. Complete removal of liquid at each step is essential to good performance. After the last wash, remove any remaining 1× Wash Buffer by aspirating or decanting. Invert the plate and blot.

Add 100 ml of prepared 1× Detection Antibody to each well. Incubate for 1 h at room temperature with shaking.

Discard the solution and wash as before.

Add 100 µl of prepared 1× HRP-conjugated anti-goat IgG to each well. Incubate for 1 hour at room temperature with shaking.

Wash as before

Add 100 µl of TMB One-Step Substrate Reagent (Item H) to each well. Incubate for 30 mins at room temperature in the dark with shaking.

Add 50 µl of Stop Solution to each well.

Read at absorbance at 450 nm immediately.

Example 2

The COVID-19 Spike-AXL binding assay uses a 96-well plate coated with recombinantly-expressed S1F. The testing reagent-of-choice is then added to the wells in the presence of recombinant human AXL protein. Unbound AXL is removed with washing, and a goat anti-AXL antibody is added that binds to the Spike-AXL complex. HRP-conjugated anti-goat IgG is then applied to the wells in the presence of 3,3',5,5'-tetramethylbenzidine (TMB) substrate. The HRP-conjugated anti-goat IgG binds to the AXL antibody and reacts with the TMB solution, producing a blue color that is proportional to the amount of bound AXL. The HRP-TMB reaction is halted with the addition of the Stop Solution, resulting in a blue-to-yellow color change. The intensity of the yellow color is then measured at 450 nm.

Materials Required:

1. COVID-19 S-protein Microplate (Item A)

96 wells (12 strips×8 wells) coated with recombinant COVID-19 S-protein RBD domain 2. Wash Buffer Concentrate (20×) (Item B)

25 ml of 20× concentrated solution 3. 5× Assay Diluent (Item E2)

15 ml of 5× concentrated buffer

This item is used to dilute the "test reagent" (that is, the potential inhibitor), AXL protein (Item F), detection antibody (Item C) and HRP-conjugated IgG Concentrate (Item D).

4. AXL protein (Item F)

2 vials of purified human recombinant AXL protein (1 vial is enough to assay half microplate)

5. Detection Antibody AXL (Item C-1)

2 vials of goat anti-AXL antibody (1 vial is enough to assay half microplate)

6. HRP-conjugated anti-goat IgG (Item D-1)

25 µl of 1000× concentrated HRP-conjugated anti-goat IgG

7. TMB One-Step Substrate Reagent (Item H)

12 ml of 3,3',5,5'-tetramethylbenzidine (TMB) in buffered solution

8. Stop Solution (Item I)

8 ml of 0.2 M sulfuric acid

The kit should be stored at 4° C. Use within 6 months from the date of shipment.

Also Required:

Microplate reader capable of measuring absorbance at 450 nm.

Shaker.

Pipettes capable of accurately delivering 2 1 to 1 ml volumes. Pipettes capable of delivering 1-25 ml volumes for reagent preparation.

Graduated cylinders: 100 ml and 1 liter

Distilled or deionized water.

Tubes to prepare sample dilutions.

Sample Preparation:

Mix "test reagent" (i.e., potential inhibitor) with AXL protein concentrate

Dilute the mixture with 1× Assay Diluent dilute to make a 1× AXL protein working concentration. Each "test reagent" sample should have the same 1× AXL protein concentration.

The optimal dilutions must be determined empirically. For the initial experiment, a serial dilution (e.g., 5-fold to 5000-fold) to determine the optimal amount of test reagent is used.

Serial Dilution Example

Using a 100 mM stock solution of the "test reagent," label and prepare 5 serial dilution tubes labeled: 20 mM, 2 mM, 0.2 mM, 0.02 mM, and 0.002 mM.

Prepare the first serial dilution tube by mixing the following together in the tube labeled "20 mM" for duplicate analyses:

50 µl of the "test reagent" stock solution
2.5 µl of AXL protein concentrate (prepared in Part VI, 4)
197.5 µl 1× Assay Diluent into the first tube labeled "20 mM".

A control should be included to account any effects that the test reagent's buffer may have on the Spike-AXL interaction. If the "test reagent" is in dimethyl sulfoxide (DMSO), for example, a parallel set of tubes should be prepared with 50 µl of DMSO.

Mix thoroughly.

Pipette 225 µl of the 1× AXL protein working solution into the remaining five labeled tubes (2 mM, 0.2 mM, 0.02 mM, 0.002 mM).

Pipette 25 µl from the prepared 20 mM tube into the second serial dilution tube (2 mM). Mix thoroughly.

Repeat step 5 for each serial dilution, using 25 µl of the prior concentration until the final concentration is reached.

Pipette 225 µl of the 1× AXL protein working solution into a separate tube labeled "0 mM." Pipette 25 µl from the 1× Assay Diluent into the tube labeled "0 mM." Mix thoroughly. This will serve as the positive control.

Reagent Preparation

Bring all reagents and samples to room temperature (18-25° C.) before use.

5× Assay Diluent (Item E2) should be diluted 5-fold with deionized or distilled water before use to make a "1× Assay Diluent."

If the Wash Concentrate (20×) (Item B) contains visible crystals, warm to room temperature and mix gently until dissolved. Dilute 20 ml of Wash Buffer Concentrate into deionized or distilled water to yield 400 ml of "1× Wash Buffer.

Briefly spin the AXL protein (Item F) before use.

Add 50 µl of 1× Assay Diluent into the Item F vial to prepare an AXL protein concentrate. Pipette up and down to mix gently.

The amount of 1× Assay Diluent that is added to Item F differs between the two Spike-AXL binding assay kit formats.

The AXL protein concentrate should be diluted 100-fold with 1× Assay Diluent to yield a "1× AXL Working Solution."

Briefly spin the Detection Antibody (Item C-1) before use. Add 100µl of 1× Assay Diluent into the vial to prepare a detection antibody concentrate. Pipette repeatedly to mix gently (the concentrate can be stored at 4° C. for 5 days or at −80° C. for one month). The goat anti-AXL antibody concentrate should be diluted 55-fold with 1× Assay Diluent and used to yield a "1× Detection Antibody" solution.

Briefly spin the HRP-conjugated anti-goat IgG (Item D-1) before use. HRP-conjugated anti-goat IgG concentrate should be diluted 1000-fold with 1× Assay Diluent to yield a "1× HRP-conjugated anti-goat IgG" solution.

Example

Briefly spin the vial to collect contents to the bottom. Add 5 □l of HRP-conjugated anti-goat IgG concentrate into a tube with 5 mL 1× Assay Diluent, then pipette repeatedly to mix gently to prepare a 1000-fold diluted HRP-conjugated anti-goat IgG solution. Mix well.

Assay Procedure

Bring all reagents to room temperature (18-25° C.) before use.

Add 100 µl of each sample into an appropriate well.

Cover with plate holder and incubate for 2.5 hours at room temperature or overnight at 4° C. with shaking.

Discard the solution and wash 4 times with 1× Wash Solution. Wash by filling each well with 1× Wash Buffer (300 µl) using a multi-channel pipette or autowasher. Complete removal of liquid at each step is essential to good performance. After the last wash, remove any remaining 1× Wash Buffer by aspirating or decanting. Invert the plate and blot.

Add 100 ml of prepared 1× Detection Antibody to each well. Incubate for 1 h at room temperature with shaking.

Discard the solution and wash as before.

Add 100 µl of prepared 1× HRP-conjugated anti-goat IgG to each well. Incubate for 1 hour at room temperature with shaking.

Wash as before

Add 100 µl of TMB One-Step Substrate Reagent (Item H) to each well. Incubate for 30 mins at room temperature in the dark with shaking.

Add 50 µl of Stop Solution to each well.

Read at absorbance at 450 nm immediately.

Example 3

AXL-S1F binding assay (Fold changes): AXL-his protein (125 ng/ml) was used to coat the wells of a micro-titer plate. After preparing the plate, S1F-his protein was added the well at different concentrations (serial dilution starting from 250 ng/ml to 7.8 ng/ml) and incubated for one hour at room temperature. After washing, mAb (Raybiotech Cat #130-10868 at 1:5000 dilution) was added and incubated for one hour followed by washing and the addition of mouse secondary antibody (at 1:5000 dilution). TMB was added and incubated for 30 min after which the absorbance at 450 nm was measured. Fold changes were calculated with respect to a S1F protein blank (i.e. without S1F) as shown in FIG. 4.

Example 4

S1F-AXL binding assay (Fold changes): S1F-his protein (125 ng/ml) was used to coat the wells of a micro-titer plate. After preparing the plate, AXL-his protein was added into the plate at different concentrations (serial dilution starting from 250 ng/ml to 7.8 ng/ml) and incubated for one hour at room temperature. After washing, mAb (R&D; Cat #MAB3870 at 1:1000 dilution) was added and incubated for one hour followed by washing and addition of mouse secondary antibody (at 1:5000 dilution). TMB was added and incubated for 30 min after which the absorbance at 450 nm was measured. Fold changes were calculated with respect to an S1F protein blank (without S1F) as shown in FIG. 4.

Example 5

SIF-AXL binding assay for determination an AXL-SIF binding inhibitor: S1F-his protein (125 ng/ml) was used to coat the wells of a micro-titer plate. After preparing the plate, AXL-his protein was added into the plate at different concentrations (serial dilution starting from 250 ng/ml to 7.8 ng/ml) and incubated for one hour at room temperature. After washing, the monoclonal antibody mAb (R&D; Cat #MAB3870 at 1:1000 dilution) was added and incubated for one hour followed by washing and addition of mouse secondary antibody (at 1:5000 dilution). TMB was added and incubated for 30 min after which the absorbance at 450 nm was measured. Parallel experiments were performed, one with the inhibitor molecule added and one without (Control).

Figure 10:
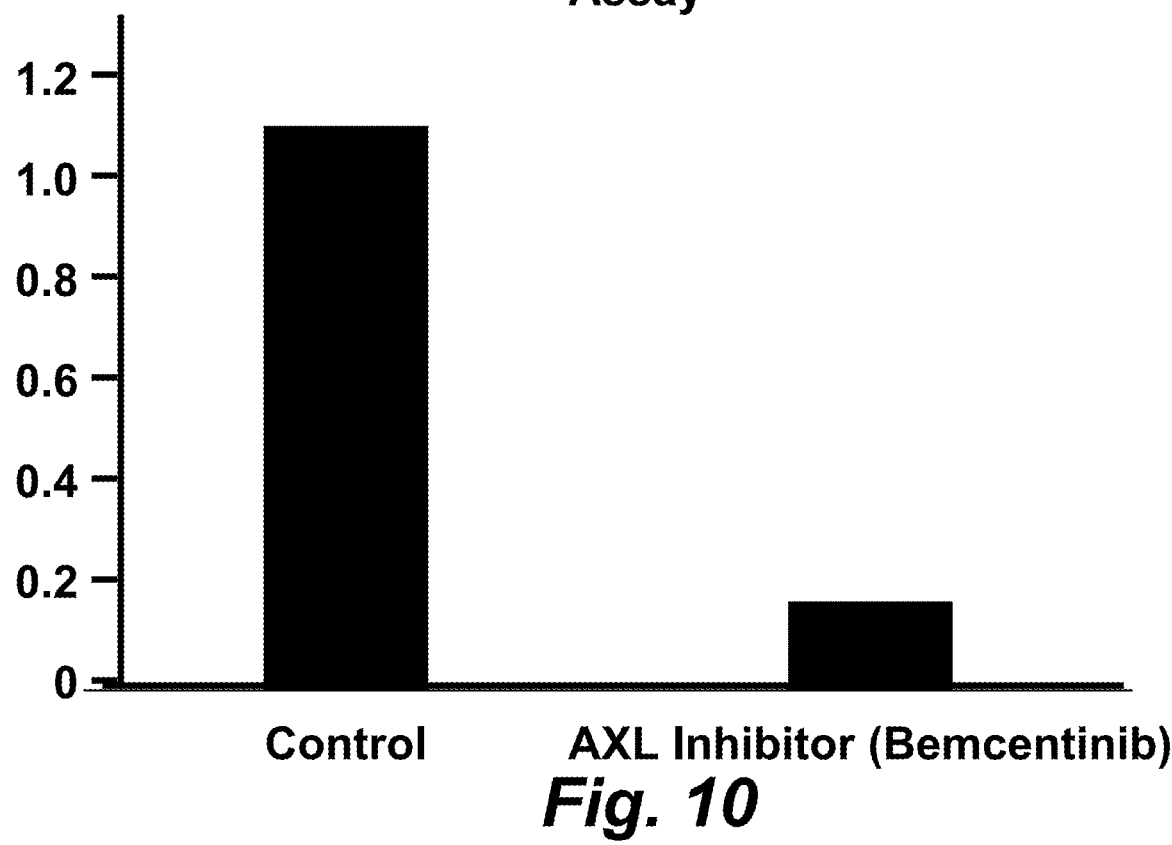
FIG. 10 illustrates the validation of the AXL-S1F binding assay using a small molecule inhibitor.

The results of adding the inhibitor Bemcentinib are shown in FIG. 10. Bemcentinib, also known as BGB324 or R428 (1H-1,2,4-Triazole-3,5-diamine 1-(6,7-dihydro-5H-benzo[6,7]cyclohepta[1,2-c]pyridazin-3-yl)-N3-[(7S)-6,7,8,9-tetrahydro-7-(1-pyrrolidinyl)-5H-benzocyclohepten-2-yl]-) is an experimental oral small molecule that is an inhibitor of AXL kinase. Bemcentinib targets and binds to the intracellular catalytic kinase domain of AXL receptor tyrosine kinase and inhibits its activity.

What is claimed:

1. A method of detecting an inhibitor of binding between the spike protein (S1F) of the SARS-CoV-2 (Covid-19) virus and tyrosine-protein kinase receptor UFO (AXL), the method comprising the steps:

(a) contacting a glycosylated S1F polypeptide with a mammalian AXL polypeptide, wherein the S1F polypeptide is bound to the wells of a microtiter plate, is a recombinant glycosylated polypeptide expressed from a mammalian cell expression system, and has the amino acid sequence SEQ ID NO: 1, and the AXL fragment has the amino acid sequence SEQ ID NO: 2 or 3;

(b) contacting the well-bound glycosylated S1F polypeptide with the AXL fragment, and then incubating the wells for a period that allows the well-bound glycosylated S1F spike protein to form a well-bound complex with the AXL fragment delivered thereto;

(c) washing the wells of unbound polypeptides;

(d) delivering to the wells from step (c) a detectably labeled anti-AXL-specific antibody;

(e) incubating the wells for a period to allow the anti-AXL-specific antibody to bind to the well-bound complex formed in step (b);

(f) washing the wells of unbound polypeptides;

(g) detecting a signal generated by the label on the anti-AXL-specific antibody bound to the well-bound complex, thereby detecting binding of the S1F polypeptide to the AXL fragment;

(h) repeating steps (a)-(g), wherein in step (a) a suspected inhibitor of S1F-AXL binding is added to the wells of the microtiter plate, wherein the suspected inhibitor is either-(1) a small molecule, a Covid-19 virus-specific antibody, or a peptide, or (2) a biological sample suspected of comprising at least one of a SARS-CoV-2 (Covid-19) virus or a Covid-19 virus-specific antibody that inhibits binding of the S1F to AXL; and (i) measuring the difference between the signals from the detectable label in the absence and presence of the suspected S1F-AXL binding inhibitor, wherein lower signal intensity generated in the presence of the suspected inhibitor compared to the signal intensity in the absence of the suspected inhibitor indicates that the suspected inhibitor is an inhibitor or comprises an inhibitor of S1F-AXL binding and the degree of the signal intensity reduction further indicates the magnitude of the inhibition.

2. The method of claim 1, wherein the label is horse radish peroxidase (HRP).

3. The method of claim 1, wherein the S1F protein and the mammalian AXL polypeptide are both glycosylated.

4. A method of detecting an inhibitor of binding between the spike protein (S1F) of the SARS-CoV-2 (Covid-19) virus and tyrosine-protein kinase receptor UFO (AXL), the method comprising the steps:
   (a) contacting a glycosylated virus spike S1F polypeptide of the SARS-CoV-2 (Covid-19) with a mammalian AXL polypeptide, thereby forming an AXL-S1F complex immobilized on the surfaces of the wells, wherein the AXL polypeptide is bound to the surfaces of wells of a microtiter plate and has the amino acid sequence SEQ ID NO: 2 or 3 and the S1F polypeptide is a recombinant glycosylated polypeptide expressed from a mammalian cell expression system, has the amino acid sequence SEQ ID NO: 1, and has a tag conjugated thereto;
   (b) washing the wells of unbound polypeptides;
   (c) delivering to the wells from step (b) a detectably labeled anti-tag-specific antibody;
   (d) incubating the wells for a period to allow the anti-tag-specific antibody delivered thereto to bind to the complex formed in step (a); and
   (e) detecting the label on the anti-tag-specific antibody bound to the complex immobilized on the microtiter plate, thereby detecting binding of the S1F to the immobilized AXL;
   (f) repeating steps (a)-(e), wherein in step (a) a suspected inhibitor of the binding of the S1F to AXL is added to the wells of the microtiter plate, wherein the suspected inhibitor is either (1) a small molecule, a Covid-19 virus-specific antibody, or a peptide, or (2) a biological sample suspected of comprising at least one of a SARS-CoV-2 (Covid-19) virus or a Covid-19 virus-specific antibody that inhibits binding of the S1F to AXL; and
   (g) measuring the difference between a signal from the detectable label in the absence and presence of the suspected inhibitor of binding of the S1F polypeptide to the AXL polypeptide, wherein a reduction in the intensity of the signal generated in the presence of the suspected inhibitor indicates that the suspected inhibitor is an inhibitor or comprises an inhibitor of S1F-AXL binding and the degree of the reduction indicates the magnitude of the inhibition.

5. The method of claim 4, wherein the tag conjugated to the S1F polypeptide is an immunoglobulin G (IgG) Fc region and the anti-tag-specific antibody is an anti-IgG Fc-specific antibody.

6. The method of claim 4, wherein the label is horse radish peroxidase (HRP).

7. The method of claim 4, wherein the S1F polypeptide and the mammalian AXL polypeptide are both glycosylated.

8. A kit comprising at least one microtiter plate comprising a plurality of wells, wherein an AXL polypeptide or a glycosylated Covid-19 virus S1F polypeptide is immobilized on the surfaces of the wells, the kit further comprising vessels containing:
   a wash buffer;
   an assay diluent;
   at least one of a glycosylated S1F polypeptide having a tag conjugated thereto and an AXL polypeptide;
   an anti-AXL polypeptide detection antibody when the S1F polypeptide is immobilized on the surfaces of the wells or an anti-tag antibody when the AXL polypeptide is immobilized on the surfaces of the wells;
   a TMB One-Step Substrate Reagent comprising 3,3',5,5'-tetramethylbenzidine (TMB) in a buffer;
   a reaction stop solution comprising about 0.2M sulfuric acid; and
   instructions for the use of the kit to assay the binding of the AXL polypeptide to the S1 FF polypeptide in the absence and presence of a compound or a biological sample suspected of inhibiting said binding.

9. The kit of claim 8, wherein the tag conjugated to the S1F polypeptide is an immunoglobulin G (IgG) Fc region and the anti-tag-specific antibody is an anti-IgG Fc-specific antibody.

* * * * *